US010729906B2

(12) United States Patent
Goldfarb et al.

(10) Patent No.: US 10,729,906 B2
(45) Date of Patent: Aug. 4, 2020

(54) MULTICHANNEL BIPHASIC SIGNAL GENERATOR CIRCUIT

(71) Applicant: VANDERBILT UNIVERSITY, Nashville, TN (US)

(72) Inventors: Michael Goldfarb, Franklin, TN (US); Kevin Ha, Nashville, TN (US); Don Truex, Murfreesboro, TN (US)

(73) Assignee: Vanderbilt University, Nashville, TN (US)

( * ) Notice: Subject to any disclaimer, the term of this patent is extended or adjusted under 35 U.S.C. 154(b) by 349 days.

(21) Appl. No.: 15/383,563

(22) Filed: Dec. 19, 2016

(65) Prior Publication Data

US 2017/0095668 A1    Apr. 6, 2017

Related U.S. Application Data

(63) Continuation of application No. PCT/US2015/036361, filed on Jun. 18, 2015.
(Continued)

(51) Int. Cl.
*A61N 1/36* (2006.01)
*A61N 1/02* (2006.01)
*A61N 1/32* (2006.01)

(52) U.S. Cl.
CPC ......... *A61N 1/36125* (2013.01); *A61N 1/025* (2013.01); *A61N 1/36003* (2013.01); *A61N 1/32* (2013.01)

(58) Field of Classification Search
None
See application file for complete search history.

(56) References Cited

U.S. PATENT DOCUMENTS 6,477,414 B1 * 11/2002 Silvian ................. A61N 1/3975
607/5
2002/0161406 A1   10/2002 Silvian
(Continued)

FOREIGN PATENT DOCUMENTS

GB          1284158 A      8/1972

OTHER PUBLICATIONS

Written Opinion of the International Searching Authority for International Application No. PCT/U7S2015/036361 dated Jan. 2015.

*Primary Examiner* — Eric D. Bertram
*Assistant Examiner* — Elizabeth K So
(74) *Attorney, Agent, or Firm* — Nixon Peabody LLP

(57) ABSTRACT

A circuit includes first and second current control sub-circuits connected in series between a DC supply voltage node and a reference voltage node and third and fourth current control sub-circuits connected in series between the DC supply voltage node and the reference voltage node. The circuit also includes a DC/DC converter with a first input terminal coupled to the first load node between the first and second current control sub-circuits, a second input terminal coupled to a second load node between the third and fourth current control sub-circuits, a first output terminal, and a second output terminal. The circuit further includes output electrodes, a routing sub-circuit for selectively coupling the output electrodes to the output terminals, and a controller configured for operating the routing sub-circuit and the current control sub-circuits to cause the DC/DC converter to supply biphasic pulses for at least one of the pairs of output electrodes.

10 Claims, 8 Drawing Sheets

Related U.S. Application Data

(60) Provisional application No. 62/013,752, filed on Jun. 18, 2014.

(56) References Cited

U.S. PATENT DOCUMENTS

| | | |
|---|---|---|
| 2003/0088279 A1 | 8/2003 | Rissman et al. |
| 2005/0278000 A1* | 12/2005 | Strother ............... A61B 5/0031 |
| | | 607/48 |
| 2015/0306407 A1* | 10/2015 | Crutchfield ............ A61N 1/385 |
| | | 607/5 |

* cited by examiner

600

700

800

MULTICHANNEL BIPHASIC SIGNAL GENERATOR CIRCUIT

CROSS-REFERENCE TO RELATED APPLICATIONS

This application is a continuation of International Patent Application No. PCT/US2015/036361, filed Jun. 18, 2015 and entitled "MULTICHANNEL BIPHASIC SIGNAL GENERATOR CIRCUIT", which claims the benefit and priority of U.S. Provisional Application No. 62/013,752, filed Jun. 18, 2014 and entitled "MULTICHANNEL BIPHASIC SIGNAL GENERATOR CIRCUIT", the contents of each of which is hereby incorporated by reference in their entirety.

FIELD OF THE INVENTION

The present invention relates to the generation of signals for multiple channels, and more specifically to apparatus and methods for generating a variety of biphasic signals for multiple channels.

BACKGROUND

A number of applications exist for the stimulation of electrically-excitable tissue. One prominent application is functional electrical stimulation (FES), by which electrical excitation is utilized to cause muscle contraction. FES can be implemented with either implanted electrodes or from skin surface electrodes. The control of muscle contraction from skin surface electrodes can be referred to as surface FES. Such control can be used to restore movement to individuals with paralysis (e.g., from spinal cord injury), or to facilitate muscle contraction in individuals with other neuromuscular impairments or injury. FES has been utilized over the past few decades to provide physiological and/or therapeutic benefits to individuals with neuromuscular impairments, and its use is currently considered a standard of care in the clinical community concerned with neuromuscular impairment. FES can be used to enable or facilitate activities such as walking, which can be referred to as FES-aided gait. In such activities, it is necessary to stimulate several muscle groups and control the output of each group independently of the other groups. For example, some combination of hip flexor, hip extensor, knee flexor, and knee extensor muscle groups must be independently controlled in order to generate walking patterns.

SUMMARY

Embodiments of the invention concern systems and methods for generating a variety of biphasic signals for multiple channels. In a first embodiment of the invention, there is provided an electronic stimulator system for generating biphasic electrical stimulation pulses. The system includes a battery and an electrical transformer with a primary winding and a secondary winding.

In the system, the primary winding is disposed between current control sub-circuits configured in an H-bridge configuration and the secondary winding of the transformer is connected to at least one pair of stimulation electrodes.

The H-bridge configuration consists of a high-side set of normally-open current control sub-circuits and a low-side set of normally-open current control sub-circuits configured in two diagonally opposing sets. The first diagonal set of normally-open current control sub-circuits includes one high-side normally-open current control element and a diagonally opposite low-side normally-open current control element. The second diagonal set of normally-open current control sub-circuits includes an opposite diagonal set of normally-open current control sub-circuits relative to the first diagonal set of normally-open current control elements. In the system, the closing the first diagonal set of normally-open current control sub-circuits directs current through the primary winding of the transformer in a first direction, and the closing the second diagonal set of normally-open current control sub-circuits directs current through the primary winding of the transformer in a second direction.

In some configurations, the high-side normally-open current control sub-circuits are switching-type control elements, and the low-side normally-open current elements are linear-type control elements, such as a variable current source. In particular, the high-side switching current control sub-circuits can be MOSFETs and the low-side linear current control sub-circuits can include bipolar junction transistors in a current source configuration. This configuration can further include two sense resistors, one corresponding to each of the first and second diagonal sets of normally-open control elements. In some configurations, a closed-loop control circuit can be provide that actively regulates the linear-type control elements in order to control the voltage across each respective sense resistor.

This configuration can operate as follow. In particular, when the high-side switching current control element corresponding to the first diagonal is momentarily closed, the corresponding low-side linear-type control element is simultaneously used to control the amplitude of the current in a first direction through the primary of the transformer. Thereafter, when the high-side switching control element corresponding to the second diagonal is momentarily closed, the corresponding low-side linear-type control element is simultaneously used to control the amplitude of current in a second direction through the primary of the transformer.

In some cases, multiple pairs of stimulation electrodes are provided and the secondary winding of the transformer is multiplexed with these multiple pairs. In one particular configuration, the secondary embodiment can be selectively connected to each pair of electrodes via a series of electronically-controllable switches, each switch corresponding to an electrode pair, such that the secondary winding of the transformer is selectively coupled to a single pair of electrodes at a given time. In some configurations, an electronic control module can be provided that varies the pulse amplitude and pulse width of each biphasic stimulation pulse as the secondary winding of the transformer is sequentially connected to each corresponding pair of stimulation electrodes.

In some configurations, the electronic control module switches between electrode pairs at a predetermined switching period, where a pulse is generated corresponding to each channel at an integer multiple of that switching period. In these configurations, the predetermined switching period is approximately determined by the product of the total number of stimulation channels and the maximum desired biphasic stimulation pulse width per channel.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
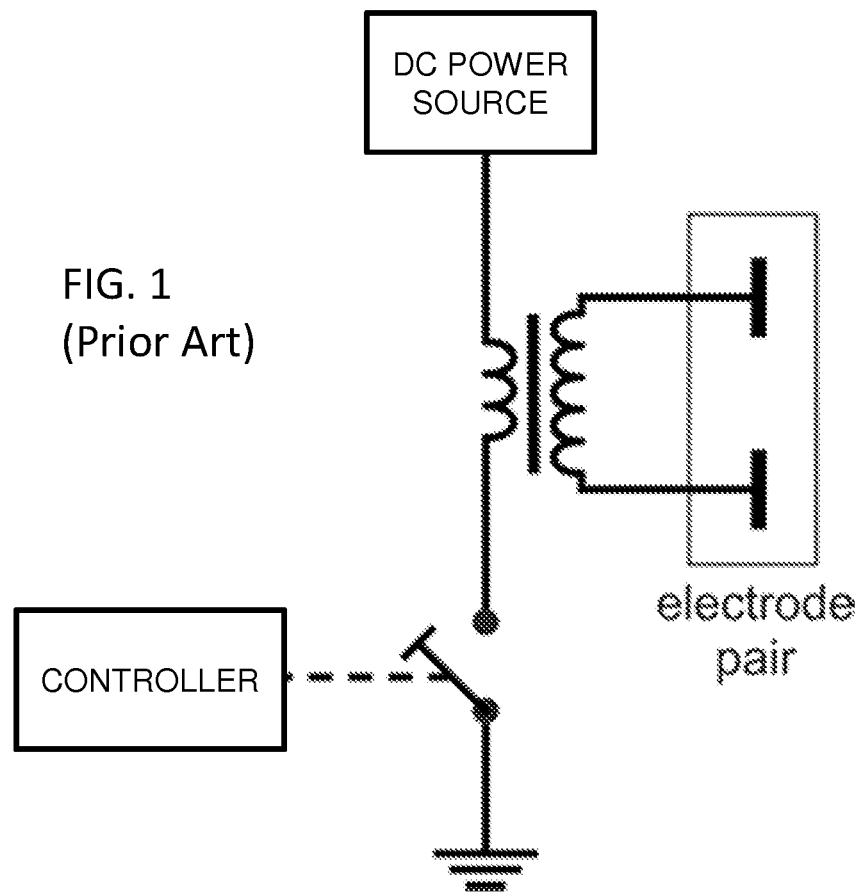
FIG. 1 shows a first configuration for a conventional stimulator circuit.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

As noted above, FES can be implemented with either implanted electrodes or from skin surface electrodes. In the latter case, an electrical stimulator creates electrical pulses between a pair of skin surface electrodes, which establishes an electrical field within the body between the electrodes. In areas between the electrodes where the current density is of sufficient strength, the electrical field may depolarize nerve fibers, thus generating action potentials in both the sensory and motor nerve fibers. The action potentials generated in the motor nerve fibers then travel to the muscle innervated by the respective fibers, which in turn generate a brief muscle contractile response corresponding to each electrical pulse. Once the nervous tissue is sufficiently depolarized, a single action potential will be generated, followed by a refractory period in which the nerve tissue must re-establish polarity across the cell membrane. Once this refractory period is complete, a subsequent pulse of electrical current is able to again depolarize the nerve fiber, and generate a subsequent action potential and corresponding muscle "twitch."

It should be noted that due to the pulsatile nature of nervous tissue, a continuous electrical field will not result in a continuous muscle contraction and multiple pulses are needed to maintain the muscle contracted. Therefore, a fused muscle contraction is established using FES by generating a continuous train of electrical pulses a sufficiently high frequency (e.g., 10 to 50 Hz, depending on the muscle characteristics) such that the muscle contraction is essentially continuous and fused (called a tetanic contraction). Note that it is desirable to stimulate a given muscle group at the lowest possible frequency that results in a fused contraction, so as to increase the endurance of the muscle.

In most cases, depolarization of a given nerve fiber is primarily a function of the amount of charge moved across the nerve fiber membrane. In turn, the amount of charge is a function of the strength of the electric field at the nerve fiber, the duration of time the field is sustained, and location and geometry of a given nerve fiber relative to the skin surface electrodes. Thus, by controlling the strength and pulse width of the field, more or fewer nerve fibers can be recruited. This results in a stronger or weaker muscle contraction, thus providing control of the strength of muscle contraction. Further, rather than controlling the voltage amplitude of each electrical pulse, it is known that controlling the current amplitude provides a more consistent and more controllable means of controlling the strength of muscle contraction. As a result, a number of factors can alter the impedance of the electrical path between the electrodes, including electrode material and condition, skin condition (i.e., moisture or sweat), and blood flow and electrolyte content in the tissue between the electrodes. Thus, by controlling the current amplitude instead of the voltage, this largely prevents these factors from significantly affecting the charge density between the electrodes and provides more consistent and predictable control of the strength of muscle contraction. Therefore, by controlling the current amplitude, pulse width, and pulse frequency of the electrical stimulation output, muscle contraction can be artificially elicited and controlled.

However, providing the necessary control of the current amplitude, pulse width, and pulse frequency of the electrical stimulation output to produce effective muscle stimulation is non-trivial. First of all, FES systems are typically required to be capable of stimulating multiple muscle groups, such as required for FES-aided gait, and therefore generally require a multichannel stimulator where each channel is independently controllable relative to the other channels. Second, because of the additional impedance involved in surface skin FES, a significant amount of power is required to ensure each channel can deliver a sufficient amount of power for muscle stimulation. Thus, conventional FES systems are typical large, bulky, and consume significant amounts of power.

Given the above-mentioned issues, the present technology provides a new electrical stimulator methodology, particularly one intended for use in surface FES, that includes (1) a capability to provide symmetric biphasic waveforms (to avoid ionic imbalance in the biological tissue over time), (2) explicit control of current amplitude in each channel, (3) explicit control of pulse width and pulse frequency, (4) multiple output channels for control of multiple stimulation sites, (5) independent control of current amplitude, pulse-width, and pulse frequency for each channel (for independent control of multiple muscle groups), (6) electrical isolation of each stimulation channel from the stimulator power supply (for the electrical safety of the individual), (7) has minimal power consumption, and (7) can be incorporated into a package of minimum size, weight, and cost, such that the stimulator is as compact, efficient, and low-cost as possible.

To this end, the present technology is directed to new stimulator circuit architecture that enables a large number of independently current-controllable output channels with a minimum amount of componentry in the power generation portion of the stimulator, which is generally the portion of the stimulator with the largest, heaviest, and most costly components. Specifically, the present technology discloses an architecture that utilizes a method of stimulation that fully exploits the output transformer in space (by utilizing the transformer at full power density) and in time (by multiplexing the output with full duty cycle), such that the net effect are smaller and lighter multichannel FES stimulator devices.

The present technology will be described primarily with respect to electrical stimulation of motor nerve fibers associated with muscle stimulation from skin surface electrodes, more generally referred to as surface functional electrical stimulation (sFES). However, the present technology is not limited in this regard. In particular, the various embodiments of the present technology can also be used for other types of stimulation, such as implantable electrical stimulation, or electrical stimulation of sensory nerves.

As previously described, sFES can provide a graded muscle contraction by exciting a variable number of motor neurons, where the variable number is essentially a function of the pulse amplitude and pulse duration (or pulse width) of the electrical field between the skin surface electrodes. Further, the consistency and predictability of response is enhanced by controlling the current amplitude of the pulse, rather than the voltage amplitude, since the former ensures a consistent charge flux across a given neuron membrane regardless of changes in skin/electrode interface impedance. For a typical stimulation pathway, full recruitment of accessible motor neurons will be achieved with pulse characteristics corresponding to pulse amplitude on the order of 100 milliamperes (mA), and a pulse width on the order of 500 micro seconds (us). Further, a fused muscle contraction requires a pulse frequency typically between 10 and 50 Hz. For sFES, skin impedance between electrodes is on the order of one kilo-Ohm. As such, the maximum required pulse characteristics are approximately 100 mA at 100 V, with a pulse duration of approximately 500 us, and with a selectable frequency between 10 Hz and 50 Hz. Since battery voltage is typically much less than 100 V, a typical electrical stimulator requires some mechanism for transforming the low-voltage battery output to a relatively high-voltage output required for stimulation.

Figure 2:
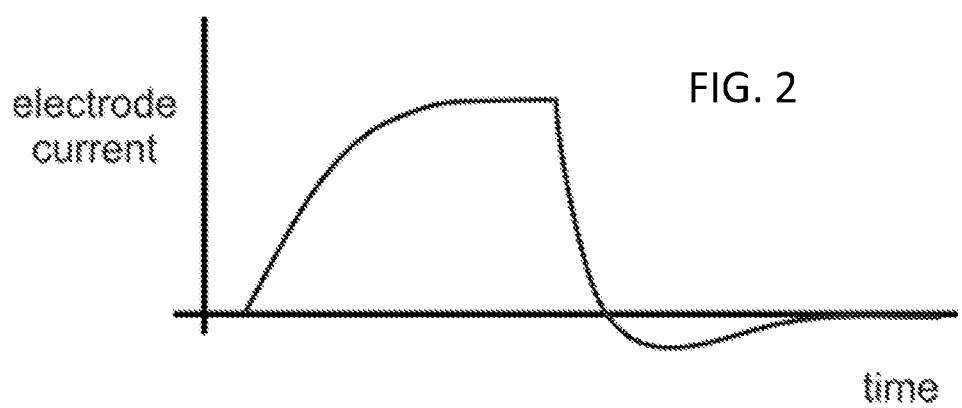
FIG. 2 shows a schematic of a monophasic pulse.

Prior to discussing the present technology in detail, it may be useful to discuss some conventional approaches to the generating of pulses for sFES. Turning first to FIG. 1, there is shown a conventional pulse-transformer-based electrical stimulator, which utilizes a transformer to convert a low-voltage, high-current pulse to a relatively high-voltage, low-current pulse. This type of stimulator will produce a monophasic pulse, such as that shown in FIG. 2. Given appropriate control circuitry (e.g., a microcontroller, transistors, etc.), the pulse transformer approach illustrated in FIG. 1 can provide monophasic pulses of a desired amplitude, width, and frequency.

Figure 3:
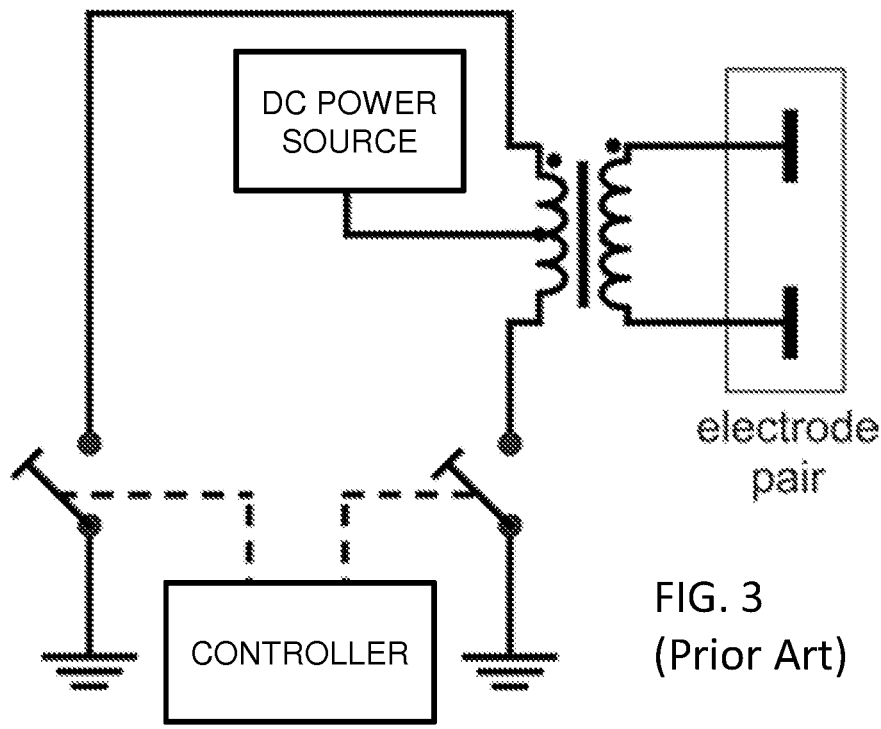
FIG. 3 shows a second configuration for a conventional stimulator circuit.
Figure 4:
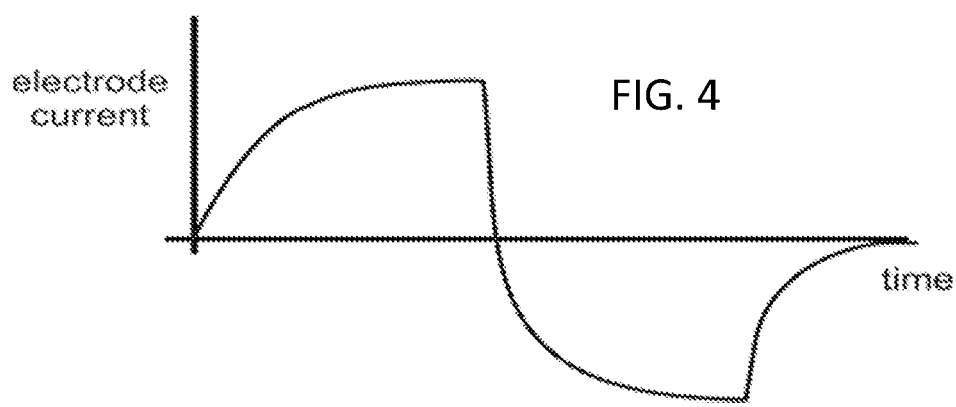
FIG. 4 shows a schematic of a biphasic pulse.
Figure 5:
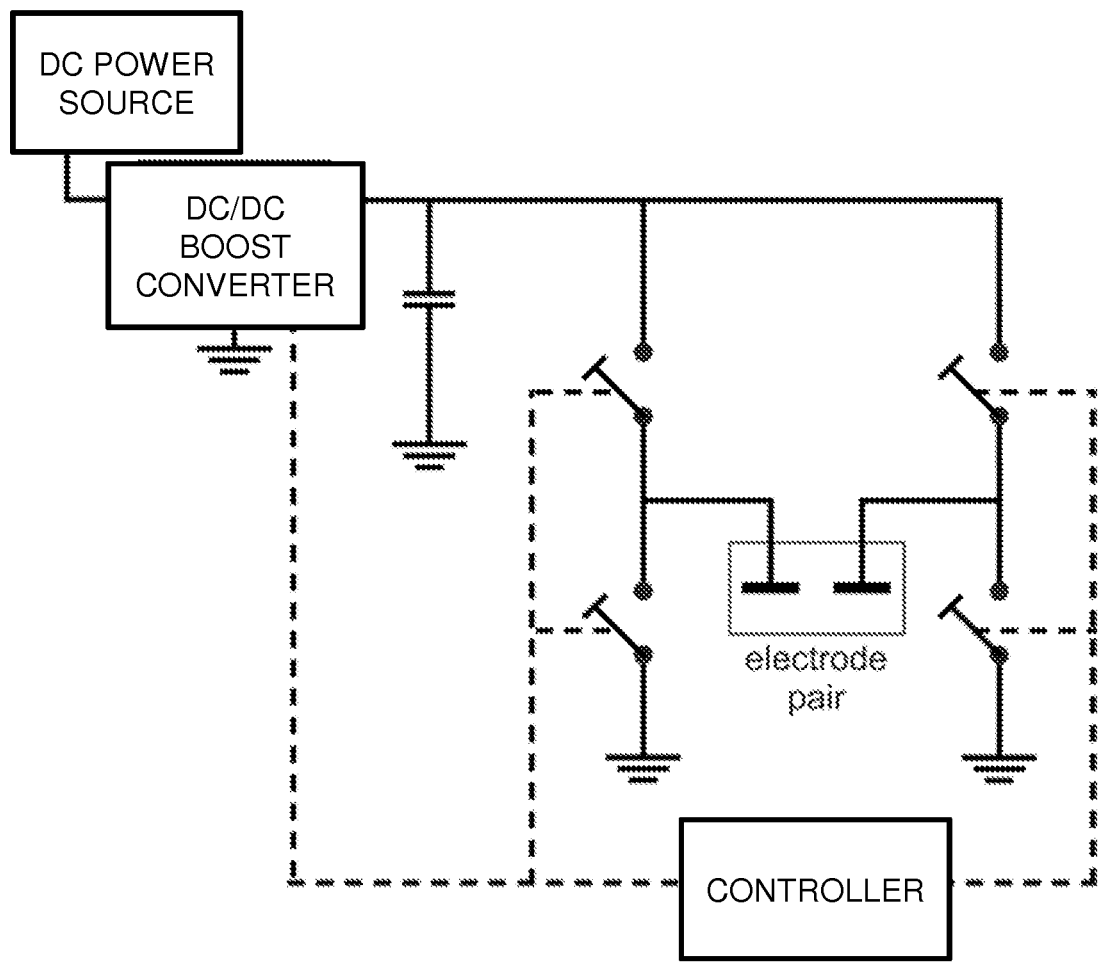
FIG. 5 shows a third configuration for a conventional stimulator circuit.

In order to provide biphasic stimulation, the use of center-tapped pulse transformers, as illustrated in FIG. 3 has been used in conventional system. In this configuration, the transformer primary contains two separate windings, and each is sequentially energized with an opposite polarity (relative to the secondary winding), such that the pulse output exhibits a biphasic character, such as shown in FIG. 4. Alternatively, rather than using pulse transformers, some conventional stimulator circuits incorporate DC/DC boost converters, as shown in FIG. 5, to charge one or more capacitors to a high voltage (i.e., a voltage appropriate for electrical stimulation) from the relatively low-voltage battery, then use an H-bridge output stage to provide a monophasic or biphasic stimulation pulse, such as those shown in FIGS. 2 and 4.

In some configurations, the pulse generation stage of a stimulator has been multiplexed to provide stimulation to multiple stimulation sites. Specifically, since stimulation pulse widths are on the order of 500 us, and pulse frequencies on the order of 50 Hz, the duty cycle of stimulation for a single channel is generally less than 5%.

In view of the limitations of the foregoing designs, the present technology provides a stimulator circuit architecture that provides biphasic stimulation appropriate for sFES with a high-density multiplexed output. Specifically, relative to a center-tapped pulse transformer, the disclosed circuit is smaller and lighter, since it fully utilizes all transformer windings during both phases of the biphasic pulse generation. Relative to DC/DC boost converter approaches, the disclosed circuit architecture eliminates charging latency, and therefore enables a higher density of multiplexed output (i.e., a greater number of output channels for comparable stimulation patterns). A further objective of the architecture of the present technology is to provide a maximum number of output channels (i.e., independent stimulation electrode pairs) with the minimum size and weight of the stimulator circuitry. Typically, the largest and heaviest elements of the conventional stimulator circuitry are the power generation stage, since this stage directly transforms power from the battery to the electrodes. During the delivery of a stimulation pulse, the pulse power is on the order of 10 W (i.e., 100 ma at 100 v at the electrodes), which is high relative to the power associated with electronic control circuitry, such as a microcontroller (which is typically on the order of 0.1 W). Therefore, the architecture allows for minimizing size and weight by minimizing the size and weight of the power generation stage.

In the case of a pulse transformer, the power density (i.e., the amount of power that the transformer can transduce from primary to secondary for a given size and weight) is generally limited by magnetic saturation. Accordingly, at some point, further increasing magnetomotive force (resulting from the primary winding) will not result in a corresponding increase in magnetic flux in the core of the transformer and therefore power will not be transferred to the output (i.e., the secondary winding). Typically, avoiding such magnetic saturation requires a larger transformer core. Since the size of the transformer is determined by flux saturation, the size of the transformer is determined by the instantaneous power requirements at the output, as opposed to the average power requirements. Therefore, if a transformer is capable of delivering a single pulse, it is also generally capable of continuously delivering similar pulses.

In the case of a center-tapped transformer, only half of the primary winding is used for the first half of the biphasic pulse (e.g., the positive portion in FIG. 4), while the other half of the primary winding is used for the second half (e.g., the negative portion in FIG. 4). As a result, the electromagnetic coupling is weaker during each portion of phase of the biphasic pulse, such that the transformer must be larger in order to accommodate the same amount of instantaneous power. In other words, the power transmission during each half of the biphasic pulse cannot exploit the full volume of transformer, and therefore the transformer cannot operate at its maximum power density. As such, for a given amount of instantaneous power transmission, the transformer must be larger than a comparable non-center-tapped version (in which the entire primary is exploited).

Although the DC/DC boost converter configuration of FIG. 5 avoids the ferrous-material-based transformer issues of the center-tapped transformer configuration, the DC/DC boost approach entails latency between stimulation pulses which limit the density of output channels when multiplexing the output. Specifically, such circuits rely on a portion of the period of dormancy between stimulation pulses to charge or discharge capacitive elements at the DC/DC convertor output, based on the desired voltage amplitude (or required voltage amplitude, in the case of current control) of the subsequent stimulation pulse. A number of trade-offs exist when multiplexing the output of this type of power generation stage. For example, if the capacitive elements are small, the elements will substantially discharge following a stimulation pulse, which will require a latency period to recharge them prior to the subsequent pulse. In contrast, if the capacitive elements are large, they require more space and also require more time to recharge to a given voltage amplitude prior to the subsequent pulse. Further, if they are large and are not substantially discharged following one stimulation pulse, and if the following pulse is intended for a channel with a much lower pulse amplitude, the capacitive element will require a period of discharge prior to the subsequent pulse, which both requires time, and presumably reduces the electrical efficiency of the circuit (i.e., presumably shunts electrical power to ground).

Unlike a DC/DC boost configuration, a pulse-transformer power generation stage does not entail latency between pulses, since there is no pre-charge or discharge period required before or after pulse delivery. As such, due to the latencies associated with boost-type stimulators, such stimulators cannot multiplex the output with as high a duty cycle as transformer-type stimulators. Therefore, a multi-channel multiplexed boost-type stimulator will in general provide fewer output channels, all other parameters being equal.

The multichannel stimulator circuit architecture of the present technology improves on conventional techniques by incorporating a pulse-transformer in an H-bridge configuration, which provides current-controllable biphasic stimulation pulses with a non-center-tapped transformer. As a result, the transformer is smaller and lighter than a center-tapped transformer-type power generation stage for the same pulse power capabilities.

Further, because the transformer does not entail latency in the pulse generation, the output can be multiplexed with maximum duty cycle (in theory 100 percent). In particular, the disclosed configuration fully exploits the output transformer both in space and in time (by avoiding the center tap and multiplexing with high duty cycle, respectively), such that the net effect is a smaller and lighter multichannel sFES stimulator, particularly when considered per channel, relative to prior art.

Figure 6:
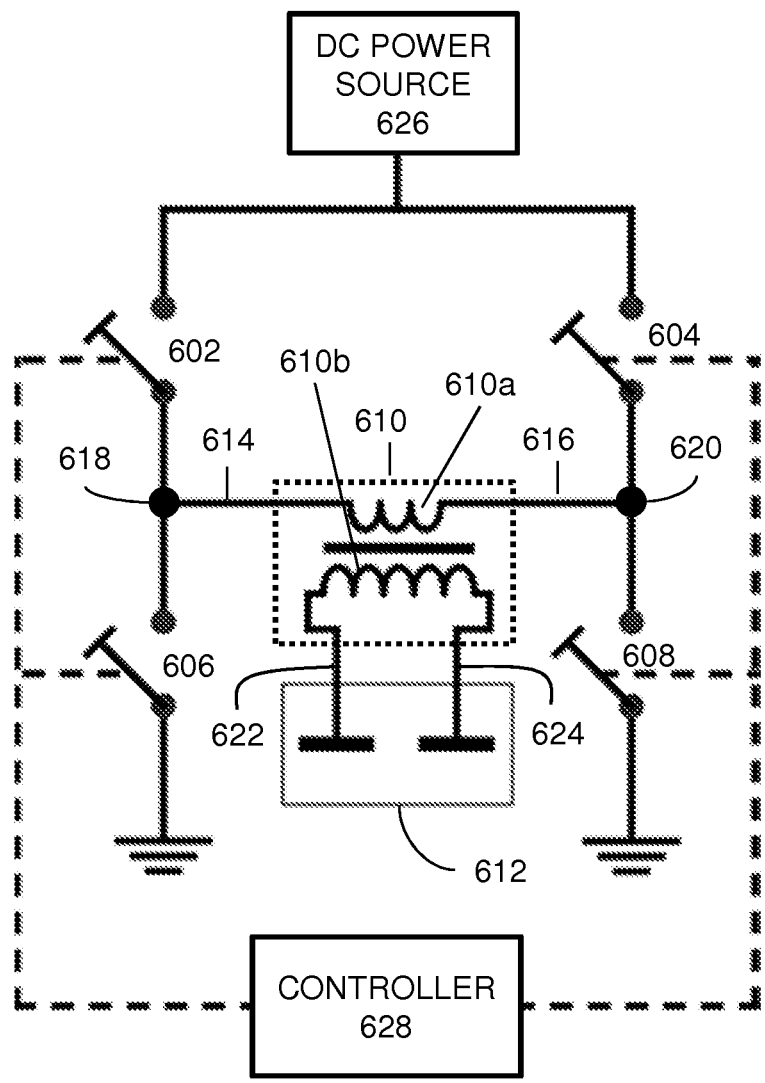
FIG. 6 shows a first exemplary configuration for a stimulator circuit in accordance with the present technology.

A basic configuration of the power generation stage in accordance with the present technology consists of a non-center-tapped pulse transformer configured within an H-bridge control circuit, as shown in FIG. 6. FIG. 6 shows an exemplary configuration for a power generation stage circuit 600 in accordance with the present technology. Circuit 600 includes current control circuits 602, 604, 606, and 608 in an H-bridge configuration with a load consisting of a transformer 610 coupled to one or more electrode pairs 612. In particular, the primary winding 610a is coupled, via input terminals 614 and 616, to load nodes 618 and 620, respectively. The secondary winding 610b is coupled via output terminals 622 and 624 to one or more electrode pairs.

In operation, the positive portion of the biphasic pulse of FIG. 4 is generated by closing a diagonal pair of the H-bridge current control sub-circuits (602 and 608) and opening the opposite diagonal pair (604 and 606). This allows current to flow from DC power source 626 to ground via high side current control circuit 602, primary winding 610a (in a first direction), and low side current control circuit 608. The negative portion of the biphasic pulse of FIG. 4 is then generated by closing the opposite diagonal pair (604 and 606) while opening the other diagonal pair (602 and 608). This allows current to flow from DC power source 626 to ground via high side current control circuit 604, primary winding 610a (in a second, opposing direction), and low side current control circuit 606. In either case, the primary winding 610a is energized. As a result, a voltage is generated across the secondary winding 610b, providing a voltage to be across terminals 622 and 624, where the polarity of the voltage is dependent on the direction of current through primary winding 610a.

The control of the biphasic pulses is provided via control of current control circuits 602, 604, 606, and 608 using a controller 628. For the positive portion of the biphasic pulse, the controller 628 provides control pulses of the desired pulse duration for the first portion of the biphasic pulse and amplitude sufficient to open a first pair of diagonal current control elements, the current control sub-circuits 602 and 608. Thereafter, to generate the negative pulse, the controller 628 applies control pulses to the opposite diagonal pair of current control sub-circuits 604 and 606. In particular embodiments, the controller can be implemented using a microcontroller, with associated peripheral electronic components.

In the present technology, the controller 628 can be implemented in a variety of ways. In some embodiments, the controller 628 can be implemented as a general purpose computing device or general purpose microcontroller, coupled to a memory which stores a computer program for causing the computing device or microcontroller to generate the control pulses or signals needed for operating the current control sub-circuits and other components described herein. Alternatively, the controller 628 can be implemented as an application specific computer device or microcontroller that is pre-configured to generate the control pulses. However, the present technology is not limited to any particular implementation for controller 628 and any other types of computing devices or microcontroller can be utilized in the present technology. The current amplitude of the biphasic pulses provided at electrodes 612 can controlled by controlling the current amplitude across the primary coil 610a. This can be implemented by configuring at least one of current control sub-circuits in each diagonal pair to allow multiple non-zero levels or amounts of current to be selected. One embodiment that enables such current control across the primary winding 610a is the circuit shown in FIG. 7.

Figure 7:
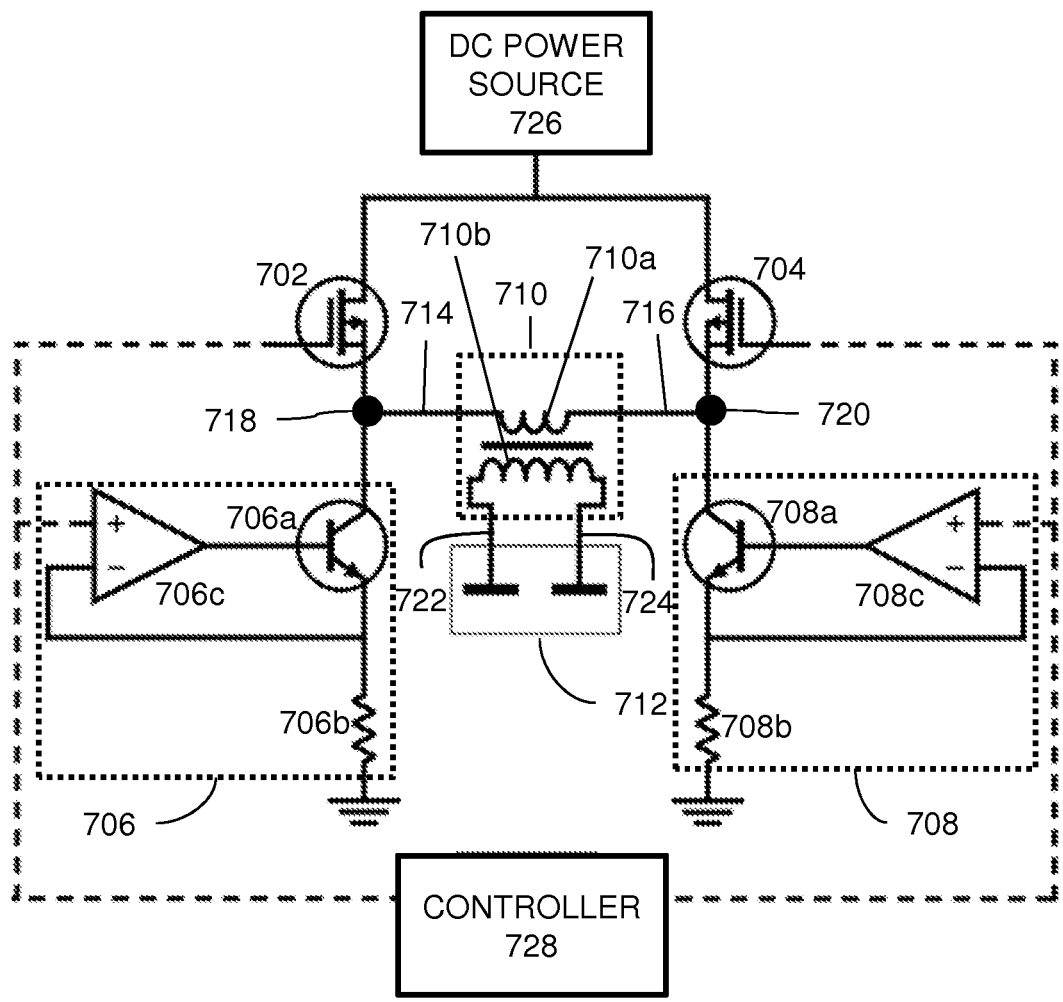
FIG. 7 shows a second exemplary configuration for a stimulator circuit in accordance with the present technology.

FIG. 7 shows an exemplary configuration for a power generation stage circuit 700 in accordance with the present technology. In FIG. 7, components 702-728 of circuit 700 generally correspond to components 602-628 of circuit 600 in FIG. 6. Accordingly, the configuration and operation of components 702-728 is substantially the same components 602-628, except where as noted below.

In this embodiment, MOSFETs are used as the high side current control sub-circuits 702 and 704. For each of the low side current control sub-circuits 706 and 708 in FIG. 7, these are configured as a variable current source. That is, they each include a bipolar junction transistor or BJT (706a, 708a) coupled in series (i.e., via collector and emitter) with a sense resistor (706b, 708b) between a load node (718, 720) and ground. An operational amplifier or op-amp (706c, 708c) is provided with an output coupled to a control node (base node) of a corresponding BJT (706a, 708a), a non-inverting input coupled to the controller 728, and an inverting input coupled to the emitter node of the corresponding BJT (706a, 708a) to provide a feedback loop.

In operation, the sense resistor (706b, 708b) is used to sense the current through the primary winding 710a during each of the positive and negative portions of the biphasic pulse, and the op-amp (708c, 708c) is used, in conjunction with control pulses from controller 728, to provide feedback control of the respective BJT (706a, 708a) to provide the desired current through the primary winding 710a. Thus, pulses of different current amplitude can be generated for electrode pairs 712 by providing control pulses from the controller 728 to the low side current control sub-circuits having varying amplitudes. This results in differences in the amplitude of current in the primary winding 710a of the transformer 710. Consequently, the amplitude of current generated in the secondary winding 710b, assuming the transformer 710 is designed to avoid saturation, would then reflect the amount of current in the primary winding 710a.

Although FIG. 7 illustrates low side current control sub-circuits 706 and 708 as a variable current source with a particular architecture, the present technology is not limited in this regard. In other embodiments, low side current control sub-circuits 706 and 708 can be implemented using any other variable current source architectures or any type of linear current control devices such that controller 728 can vary the amount of current flowing through primary winding 710a.

As noted above, the output of the transformer can be multiplexed into a plurality of stimulation electrode pairs. In this embodiment, the output terminals of a secondary winding of a transformer can be sequentially connected to each subsequent pair of electrodes via electrically-controllable switches. This is illustrated in FIG. 8.

Figure 8:
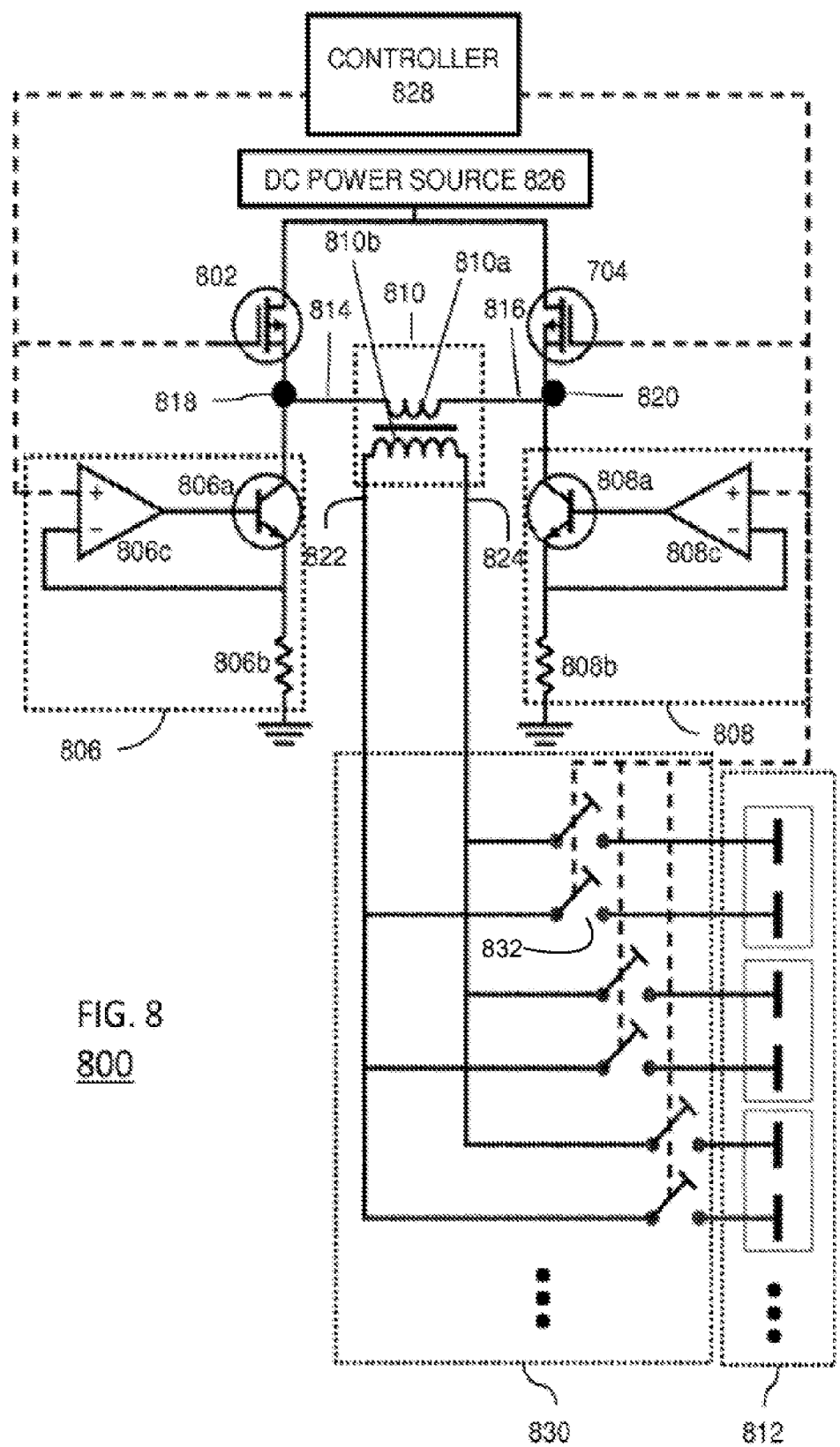
FIG. 8 shows the configuration of FIG. 7 adapted to route signals to a different pairs of electrodes.

FIG. 8 shows an exemplary configuration for a power generation stage circuit 800 in accordance with the present technology. In FIG. 8, components 802-828 of circuit 800 generally correspond to components 702-728 of circuit 700 in FIG. 7. Accordingly, the configuration and operation of components 802-828 is substantially the same as that of components 702-728, except where as noted below.

As noted above, one or more electrode pairs 812 can be provided. However, in some cases it is preferable to stimulate the different pairs of electrodes 812 differently. For example, different types of muscle groups can require different stimulation pulses. Accordingly, a routing circuit 830 can be provided to route or multiplex the signal at output terminals 822 and 824 to different ones of pairs of electrodes 812. As shown in FIG. 8, the routing circuit 830 can include a series of switch pairs 832, where each of the switch pairs corresponds to a different one of the electrode pairs 812. The switch pairs 832 can also be controlled via controller 828. In operation, the controller 828 can therefore provide control pulses that specify not only the amplitude and duration of the biphasic pulses to be generated, but also to which one of pairs of electrodes 812 is to receive a particular pulse.

Since the pulse generation of the present technology entails no substantial latency, a large number of channels (i.e., electrode pairs receiving different biphasic pulses) can be accommodated based on the maximum duty cycle of a given channel. That is, the maximum pulse width required and the frequency at which such a pulse width is required. For example, if the highest duty cycle channel for a given interval of time is 5 percent, the single-transformer stimulator of the present technology can provide 20 channels of stimulation, each capable of a duty cycle of up to 5 percent. Further, since the current amplitude and pulse width can be controlled instantaneously (e.g., by the op-amp-based feedback loop of FIGS. 7 and 8), the amplitude and width of each stimulation channel can be controlled fully independently of other channels, without latency between channels.

While the frequency of stimulation of each channel cannot be controlled entirely independently, for most practical purposes the frequency of stimulation can be controlled with sufficient independence. For example, if the maximum pulse width for a channel is 500 us, each successive pulse could be generated every 500 us. That is, at a frequency of 2 kHz (i.e., new pulses generated at a period of 0.5 ms). If the stimulator supports 10 output channels, then the stimulator can generate a new pulse at each channel with a minimum period of 5 ms. Further, since the control system can connect each channel to the secondary of the transformer independently, each can be connected to the secondary at a period that is an integer multiple of the minimum period. As a result, each channel can be assigned an independent frequency of $1/(T*x)$ Hz, where T is the minimum period and x is an integer greater than or equal to one representing the number of period between multiplexing a given channel or set of electrodes. For the example above, the frequency is frequency of $1/(0.005x)$ Hz Accordingly, each channel can independently select a frequency between about 1 Hz (x=200) and 200 Hz (x=1), which provides more than sufficient resolution in pulse frequency, particularly in the 10 to 40 Hz range, for typical sFES applications (e.g., provides 16 frequencies in the range of 10 to 40 Hz).

EXAMPLES

The following examples and results are presented solely for illustrating the various embodiments and are not intended to limit the various embodiments in any way.

To verify the ability of the circuit architecture of the present technology to provide a useful set of output pulses, the circuit of FIG. 8 was constructed and tested for a four channel configuration. In this setup, an 80 MHz 32-bit microcontroller was used as controller 828, and a one kilo-Ohm resistor was placed across each electrode pair 812 to simulate skin load. In order to demonstrate the ability of the stimulator to generate four channels of stimulation with independently-controllable stimulation characteristics, the stimulator was configured to generate the following characteristics in each of the four channels of electrical stimulation:

Channel 1 was commanded to have an amplitude of 30 mA and a frequency of 25 Hz;
Channel 2 to have an amplitude of 40 mA and a frequency of 50 Hz;
Channel 3 an amplitude of 50 mA and a frequency of 25 Hz; and
Channel 4 an amplitude of 60 mA and a frequency of 50 Hz.

In this example, all pulses were configured with a pulse width of 200 microseconds.

Figure 9A:
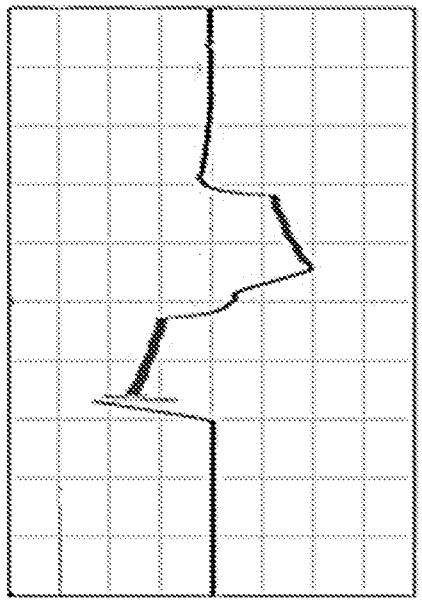
FIGS. 9A, 9B, 9C, and 9D show oscilloscope captures of signals from different channels of a four channel stimulator circuit in accordance with the present technology.
Figure 9B:
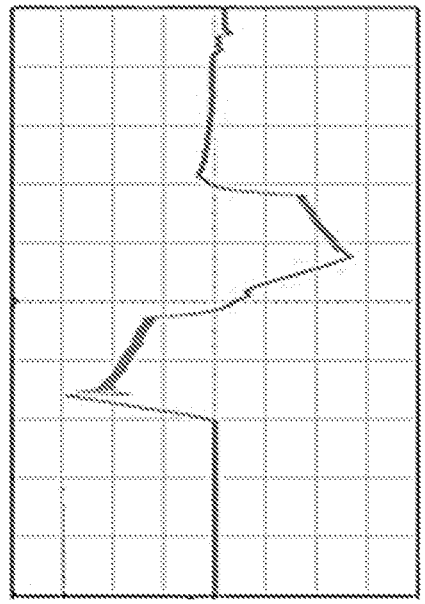
Figure 9C:
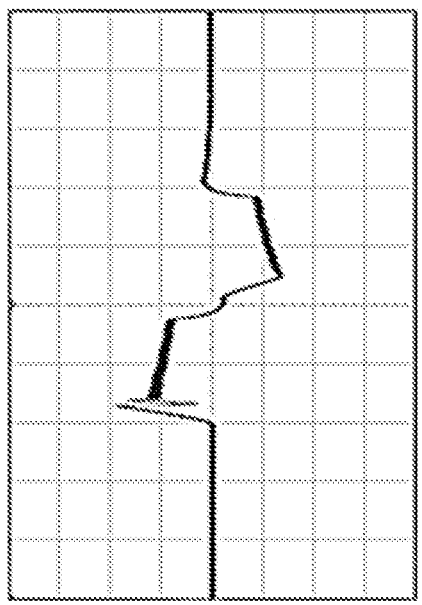
Figure 9D:
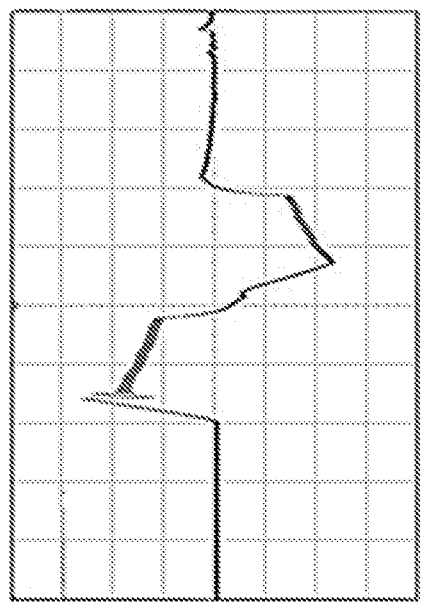

FIGS. 9A-9D, 10, and 11 show oscilloscope screen captures of the biphasic stimulator output for the configuration described above. Specifically, FIGS. 9A-9D shows close-ups of each pulse for each of channels 1-4, respectively, with each scope trace characterized by an amplitude scaling of 20 mA per division (i.e., 20V per division across a 1 kilo Ohm resistor) and a time scaling of 50 microseconds per division. As such, the initial peak of channel 1 is at approximately 30 mA (as shown in FIG. 9A), the initial peak of channel 2 at approximately 40 mA (as shown in FIG. 9B), the initial peak of channel 3 at approximately 50 mA (as shown in FIG. 9C), and the initial peak of channel 4 at approximately 60 mA (as shown in FIG. 9D)

Figure 10:
FIG. 10 shows an oscilloscope capture of signals from a four channel stimulator circuit in accordance with the present technology in a first configuration.

FIG. 10 shows the same output shown in FIGS. 9A-9D, but shows the sequence of all four channels in time over a single output cycle (where the amplitude scaling represents 50 mA per division and time scaling 2 milliseconds per division). As shown in FIG. 10, the stimulator of the present technology is capable of producing these pulses without latency between them, although in this case, they are spaced evenly.

Figure 11:
FIG. 11 shows an oscilloscope capture of signals from a four channel stimulator circuit in accordance with the present technology in a second configuration.

FIG. 11 shows the same output as shown in FIG. 10, but with over twice the time period (i.e., two cycles of two cycles of the four-channel output), showing that the pulse frequency of channels 2 and 4 is twice the pulse frequencies of channels 1 and 3 (i.e., 50 and 25 Hz, respectively), thus illustrating the ability of the stimulator to provide different pulse frequencies on different channels. Because the duty cycle of stimulation in general is low (i.e., typically a few percent), the pulses become quite narrow and difficult to see when shown over multiple cycles of stimulation.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. Also, the terms "about", "substantially", and "approximately", as used herein with respect to a stated value or a property, are intend to indicate being within 20% of the stated value or property, unless otherwise specified above. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method for generating biphasic electrical stimulation pulses comprising:
providing an H-bridge circuit comprising first and second current control sub-circuits connected in series between a DC supply voltage node and a reference voltage node, third and fourth current control sub-circuits connected in series between the DC supply voltage node and the reference voltage node, and a transformer with a first input terminal coupled to a first load node between the first and the second current control sub-circuits and a second input terminal coupled to a second load node between the third and the fourth current control sub-circuits, wherein the first and the third current control sub-circuits comprise high-side current control circuits and wherein the second and the fourth current control sub-circuits comprise low-side current control circuits;
operating the first, the second, the third, the fourth current control sub-circuits to generate a biphasic pulse, the operating comprising:
closing the first and the fourth current control sub-circuits and opening the second and the third current control sub-circuits circuit to cause a current from the DC power supply voltage to be directed through the transformer in a first direction to generate a first portion of a biphasic pulse with a first polarity, and
closing the second and the third current control sub-circuits and opening the first and the fourth current control sub-circuits circuit to cause a current from the DC power supply voltage to be directed through the transformer in a second direction to generate a second portion of a biphasic pulse with a second polarity; and
selectively coupling output terminals of the transformer to one of a plurality of pairs of electrodes to deliver the first and the second portions of the biphasic pulse to the one of the plurality of electrode pairs.

2. The method of claim 1, wherein the transformer comprises a non-center-tapped pulse transformer, wherein the first and the second input terminals are coupled to a primary winding of the transformer, wherein output terminals are coupled to a secondary winding of the transformer.

3. The method of claim 1, wherein the first and the third current control sub-circuits are switching-type sub-circuits, and wherein the second and the fourth current control sub-circuits are variable current control sub-circuits, and wherein the operating comprises limiting an amount of current through the input terminals of the transformer.

4. The method of claim 3, wherein the switching-type sub-circuits comprise MOSFETs, and wherein the variable current control sub-circuits comprise bipolar junction transistors.

5. The method of claim 4, wherein the variable current control sub-circuits comprises sense resistors configured to sense the current through a primary winding of the transformer, and wherein the operating further comprising regulating the second and the fourth current control sub-circuits to control the voltage across each respective sense resistor.

6. The method of claim 3, wherein at least one of the first and the third current control sub-circuits are configured to allow multiple amounts of current and at least one of the second and the fourth current control sub-circuits are configured to allow multiple amounts of current, and wherein the operating further comprises selecting the amount of current to control an amplitude for the first and the second portions of the biphasic pulse.

7. The method of claim 1, wherein the at least one pair of stimulation electrodes comprises multiple pairs of electrodes, and wherein the output terminals of the transformer are sequentially coupled to each pair of electrodes so that the output terminals of the transformer are coupled to a single one of the pair of electrodes at a time.

8. The method of claim 7, wherein the operating selectively closing the second and the fourth current control sub-circuits such that at least one of an amplitude and a width of the biphasic pulse is different for at least two of the multiple pairs of electrodes.

9. The method of claim 7, wherein the selectively coupling comprises switching between the multiple pairs of electrodes at a predetermined switching period, and wherein the biphasic pulse for each of the multiple pairs of electrodes is generated at a time corresponding to an integer multiple of predetermined switching period.

10. The method of claim 9, wherein the predetermined switching period comprises a product of the total number of the multiple electrode pairs and the maximum biphasic stimulation pulse.

* * * * *